United States Patent [19]
Vogel et al.

[11] Patent Number: 5,798,107
[45] Date of Patent: Aug. 25, 1998

[54] WRINKLE REDUCING COMPOSITION

[75] Inventors: Alice Marie Vogel, Middletown; Errol Hoffman Wahl; Jerome Paul Cappel, both of Cincinnati, all of Ohio; Thomas Carl Ward, Blacksburg, Va.

[73] Assignee: The Procter & Gamble Company, Cincinnati, Ohio

[21] Appl. No.: 668,978

[22] Filed: Jun. 24, 1996

Related U.S. Application Data

[63] Continuation of Ser. No. 338,314, Nov. 10, 1994, abandoned.

[51] Int. Cl.$^6$ ........................................... A61K 9/00
[52] U.S. Cl. ................... 424/400; 424/402; 222/632; 252/8.6
[58] Field of Search .................... 424/402, 400; 222/632; 252/8.6

[56] References Cited

U.S. PATENT DOCUMENTS

| | | | |
|---|---|---|---|
| 2,789,379 | 4/1957 | Edwards et al. | 38/144 |
| 2,826,551 | 3/1958 | Geen | 252/89 |
| 3,436,772 | 4/1969 | Stebbins | 8/149.2 |
| 3,600,325 | 8/1971 | Kaufman et al. | 252/305 |
| 3,674,688 | 7/1972 | Schwartz et al. | 252/8.8 |
| 3,833,393 | 9/1974 | Kandathil | 106/212 |
| 3,896,032 | 7/1975 | Stroh et al. | 252/8.6 |
| 3,964,500 | 6/1976 | Drakoff | 132/7 |
| 4,082,223 | 4/1978 | Nozawa | 239/333 |
| 4,248,590 | 2/1981 | Koerner et al. | 8/128 |
| 4,260,110 | 4/1981 | Werding | 239/404 |
| 4,274,560 | 6/1981 | Cater | 222/321 |
| 4,283,191 | 8/1981 | Koerner et al. | 8/128 |
| 4,419,391 | 12/1983 | Tanaka et al. | 427/387 |
| 4,434,917 | 3/1984 | Saito et al. | 222/383 |
| 4,541,936 | 9/1985 | Ona et al. | 252/8.6 |
| 4,661,267 | 4/1987 | Dekker et al. | 252/8.8 |
| 4,661,268 | 4/1987 | Jacobson et al. | 252/8.8 |
| 4,711,730 | 12/1987 | Gosselink et al. | 252/8.75 |
| 4,735,347 | 4/1988 | Schultz et al. | 222/321 |
| 4,749,596 | 6/1988 | Evans et al. | 427/242 |
| 4,756,850 | 7/1988 | Nayar | 252/547 |
| 4,800,026 | 1/1989 | Coffindaffer et al. | 252/8.8 |
| 4,806,254 | 2/1989 | Church | 252/8.6 |
| 4,818,569 | 4/1989 | Trinh et al. | 427/242 |
| 4,819,835 | 4/1989 | Tasaki | 222/383 |
| 4,877,896 | 10/1989 | Maldonado et al. | 560/14 |
| 4,895,279 | 1/1990 | Schultz | 222/321 |
| 4,911,852 | 3/1990 | Coffindaffer et al. | 252/8.8 |
| 4,911,853 | 3/1990 | Coffindaffer et al. | 252/8.8 |
| 4,923,623 | 5/1990 | Coffindaffer | 252/8.8 |
| 4,956,447 | 9/1990 | Gosselink et al. | 528/272 |
| 4,976,879 | 12/1990 | Maldonado et al. | 252/8.7 |
| 5,064,543 | 11/1991 | Coffindaffer et al. | 252/8.6 |
| 5,100,566 | 3/1992 | Agbomeirele et al. | 252/86 |
| 5,111,971 | 5/1992 | Winer | 222/95 |
| 5,232,126 | 8/1993 | Winer | 222/95 |

FOREIGN PATENT DOCUMENTS

| | | | |
|---|---|---|---|
| 0 058 493 A1 | 8/1982 | European Pat. Off. | D06M 15/66 |
| 0 190 839 A2 | 8/1986 | European Pat. Off. | D06M 13/46 |
| 0 354 856 A2 | 2/1990 | European Pat. Off. | C11D 3/37 |
| 1 549 180 | 7/1979 | United Kingdom | C08L 83/04 |

OTHER PUBLICATIONS

"Anelastic and Dielectric Effects in Polymeric Solids". N. G. McCrum et al., Dover Publications, Inc., 1967.

*Primary Examiner*—Thurman K. Page
*Assistant Examiner*—D. Faulkner
*Attorney, Agent, or Firm*—Robert B. Aylor

[57] ABSTRACT

The present invention relates to a wrinkle reducing composition for use on fabrics, particularly clothing. The composition comprises a wrinkle reducing active, which is made up of an effective amount of silicone and an effective amount of film-forming polymer, and a liquid carrier. The composition is substantially free of starch, modified starch, and mixtures thereof, and results a Loss Modulus Difference of greater than about $3.3 \times 10^7$ Pascal on fabric. The composition can be incorporated into a spray dispenser that can create an article of manufacture which facilitates treatment of the fabric with the wrinkle reducing composition. The wrinkle reducing actives in the composition can be determined through Dynamic Mechanical Analysis using a 100% cotton broadcloth swatch and a fixed volume of a sample of wrinkle reducing active.

33 Claims, No Drawings

WRINKLE REDUCING COMPOSITION

CROSS-REFERENCE TO RELATED APPLICATION

This application is a file wrapper continuation of our application Ser. No. 08/338,314, filed Nov. 10, 1994, now abandoned.

TECHNICAL FIELD

The present invention relates to fabric care compositions and to a method for treating fabrics in order to improve various properties of fabrics, in particular, reduction or removal of unwanted wrinkles.

BACKGROUND OF THE INVENTION

Wrinkles in fabrics are caused by the bending and creasing of the textile material which places an external portion of a filament in a yarn under tension while the internal portion of that filament in the yarn is placed under compression. Particularly with cotton fabrics, the hydrogen bonding that occurs between the cellulose molecules contributes to keeping wrinkles in place. The wrinkling of fabric, in particular clothing, is therefore subject to the inherent tensional elastic deformation and recovery properties of the fibers which constitute the yarn and fabrics.

In the modern world, with the increase of hustle and bustle and travel, there is a demand for a quick fix which will help to diminish the labor involved in home laundering and/or the cost and time involved in dry cleaning or commercial laundering. This has brought additional pressure to bear on textile technologists to produce a product that will sufficiently reduce wrinkles in fabrics, especially clothing, and to produce a good appearance through a simple, convenient application of a product.

The present invention reduces wrinkles from fabrics, including clothing, dry cleanables, and draperies, without the need for ironing. The present invention can be used on damp or dry clothing to relax wrinkles and give clothes a ready to wear look that is demanded by today's fast paced world. The present invention also essentially eliminates the need for touch up ironing usually associated with closet, drawer, and suitcase storage of garments.

When ironing is desired however, the present invention can also act as an excellent ironing aid. The present invention makes the task of ironing easier and faster by creating less iron drag. When used as an ironing aid, the composition of the present invention produces a crisp, smooth appearance similar to that of spray starch ironing aids without the dry residue or flaking that occurs with typical spray starch ironing aids An additional benefit of the composition of the present invention is an in-wear wrinkle control benefit. The composition of the present invention can help to prevent future wrinkles from forming in the fabric even after the fabric has been through a wash cycle.

SUMMARY OF THE INVENTION

The present invention relates to a wrinkle reducing composition, comprising:

A. a wrinkle reducing active, comprising:
1. an effective amount of silicone;
2. an effective amount of film-forming polymer; and
B. a liquid carrier; and wherein said wrinkle reducing active is substantially free of starch, modified starch, and mixtures thereof, and wherein said wrinkle reducing composition results in a Loss Modulus Difference, as described hereinafter, of greater than about $3.3 \times 10^7$ Pascal on fabric and/or a Durable Press Grade of from about 3.3, to about 4.8 on fabric.

DETAILED DESCRIPTION OF THE INVENTION

The present invention relates to a wrinkle reducing composition, comprising:

A. a wrinkle reducing active, comprising:
1. an effective amount of silicone;
2. an effective amount of film-forming polymer; and
B. a liquid carrier; and wherein said wrinkle reducing active is substantially free of starch, modified starch, and mixtures thereof, and wherein said wrinkle reducing composition results a Loss Modulus Difference of greater than about $3.3 \times 10^7$ Pascal on fabric.

A. WRINKLE REDUCING ACTIVES

I. SILICONE

The present invention, in one aspect, uses silicone to impart a lubricating property or increased gliding ability to fibers in fabric, particularly clothing.

Any type of silicone can be used to impart the lubricating property of the present invention however, some silicones and mixtures of silicones are more preferred. The word "silicone" as used herein refers to emulsified silicones, including those that are commercially available and those that are emulsified in the composition, unless otherwise described. Some non-limiting examples of silicones which are useful in the present invention are: Non-volatile silicone fluids such as polydimethylsiloxane gums and fluids, aminosilicones, reactive silicones and phenylsilicones. More specifically, materials such as polyalkyl or polyaryl silicones with the following structure:

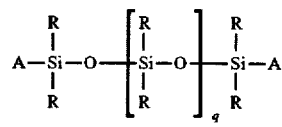

The alkyl or aryl groups substituted on the siloxane chain (R) or at the ends of the siloxane chains (A) can have any structure as long as the resulting silicones remain fluid at room temperature. Preferably, the silicones are hydrophobic, are neither irritating, toxic, nor otherwise harmful when applied to fabric or when they come in contact with human skin, are compatible with other components of the composition, are chemically stable under normal use and storage conditions, and are capable of being deposited on fabric.

The R group preferably is a phenyl, a hydroxy, an alkyl or an aryl. The two R groups on the silicone atom can represent the same group or different groups. More preferably, the two R groups represent the same group preferably, a methyl, an ethyl, a propyl, a phenyl or a hydroxy group. q is preferably an integer from about 7 to about 8,000.

"A" represents groups which block the ends of the silicone chains. Suitable A groups include hydrogen, methyl, methoxy, ethoxy, hydroxy, propoxy, and aryloxy. The preferred silicones are polydimethyl siloxanes; more preferred silicones are polydimethyl siloxanes having a viscosity of greater than about 10,000 centistokes (cst) at 25° C.; and a most preferred silicone is a reactive silicone, i.e., where A is an OH group.

Suitable methods for preparing these silicone materials are disclosed in U.S. Pat. Nos. 2,826,551 and 3,964,500, incorporated herein by reference. Silicones useful in the present invention are also commercially available. Suitable examples include silicones offered by Dow Corning Corporation.

Other useful silicone materials include materials of the formula:

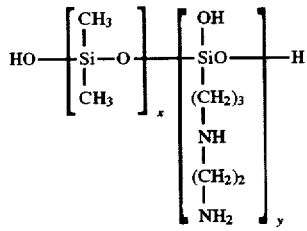

wherein x and y are integers which depend on the molecular weight of the silicone, the viscosity being from about 10,000 (cst) to about 500,000 (cst) at 25° C. This material is also known as "amodimethicone". Although silicones with a high number, e.g., greater than about 0.5 millimolar equivalent of amine groups can be used, they are not preferred because they can cause fabric yellowing.

Other silicone materials which can be used, but are not preferred, correspond to the formulas:

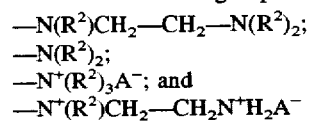

wherein G is selected from the group consisting of hydrogen, phenyl, OH, and/or $C_1$–$C_8$ alkyl; a denotes 0 or an integer from 1 to 3; b denotes 0 or 1; the sum of n+m is a number from 1 to about 2,000; $R^1$ is a monovalent radical of formula $C_pH_{2p}L$ in which p is an integer from 2 to 8 and L is selected from the group consisting of:

—N($R^2$)$CH_2$—$CH_2$—N($R^2$)$_2$;
—N($R^2$)$_2$;
—$N^+$($R^2$)$_3$$A^-$; and
—$N^+$($R^2$)$CH_2$—$CH_2N^+H_2A^-$ wherein each $R^2$ is chosen from the group consisting of hydrogen, phenyl, benzyl, a saturated hydrocarbon radical, and each $A^-$ denotes compatible anion, e.g., a halide ion; and

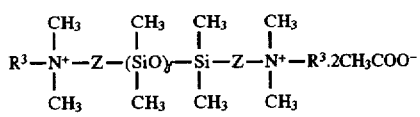

wherein

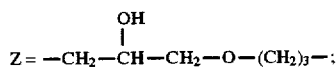

$R^3$ denotes a long chain alkyl group; and
f denotes an integer of at least about 2.

In the formulas herein, each definition is applied individually and averages are included.

Another silicone material which can be used, but is not preferred, has the formula:

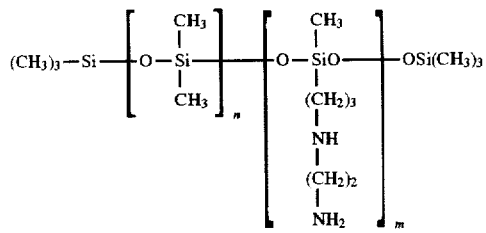

wherein n and m are the same as before.

Alternatively, the silicone material can be provided by a single material. Examples of such materials are copolymers having siloxane macromers grafted thereto, which meet the functional limitations as defined above. That is, the non-silicone backbone of such polymers should have a molecular weight of from about 5,000 to about 1,000,000, and the polymer should have a glass transition temperature (Tg), i.e., the temperature at which the polymer changes from a brittle vitreous state to a plastic state, of greater than about −20° C. This material is not preferred when the carrier is more than about 95% water.

The silicones used in the present invention typically have a viscosity of from about 1,000 (cst) to about 2,000,000 (cst), preferably from about 1,000 (cst) to about 1,500,000 (cst), more preferably from about 1,000 (cst) to about 1,000,000 (cst).

When silicone is present, it is present at least an effective amount to provide lubrication of the fibers, typically from about 0.1% to about 4.5%, preferably from about 0.2% to about 4.0%, more preferably from about 0.3% to about 3.0%, by weight of the composition. Silicones present at levels higher than about 4.5%, by weight of the composition are not preferred because they can cause oil spots to appear on the fabric.

II. FILM-FORMING POLYMER

The present invention, in one aspect, uses film-forming polymer to impart shape retention to fabric, particularly clothing. Any type of film-forming polymer can be used to impart shape retention however, some film-forming polymers are more preferred. The film-forming polymers useful in the present invention are comprised of monomers. Some nonlimiting examples of monomers which can be used to form the film-forming polymers of the present invention include: adipic acid; ethenyl formamide; diethylene triamine; vinyl amine; acrylic acid; methacrylic acid; N,N-dimethylacrylamide; N-t-butyl acrylamide; maleic acid; maleic anhydride, and its half esters; crotonic acid; itaconic acid; acrylamide; acrylate alcohols; hydroxyethyl methacrylate; vinyl pyrrolidone; vinyl ethers (such as methyl vinyl ether); maleimides; vinyl pyridine; vinyl imidazole and other polar vinyl heterocyclics; styrene sulfonate; allyl alcohol; vinyl alcohol (produced by the hydrolysis of vinyl acetate after polymerization); vinyl caprolactam; acrylic or methacrylic acid esters of $C_1$–$C_{18}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, and the like, the alcohols having from about 1–18 carbon atoms with the average number of carbon atoms being from about 4 to about 12; styrene; polystyrene macromer; vinyl acetate; vinyl chloride; vinylidene chloride; vinyl propionate; alphamethylstyrene; t-butylstyrene; butadiene; cyclohexadiene; ethylene; propylene; vinyl toluene; methoxy ethyl methacrylate; and mixtures thereof. Preferably, said monomers are selected from the group consisting of vinyl alcohol; vinylpyrrolidone; acrylic acid; dimethylaminoethyl methacrylate; ethyl acrylate; methyl methacrylate; methacrylic acid; diethylenetriamine; vinyl pyridine; adipic acid; and mixtures thereof.

Preferably, said monomers form homopolymers and/or copolymers (i.e., the film-forming polymer) having a glass transition temperature (Tg) of from about −20° C. to about 150° C., preferably from about −10° C. to about 150° C., more preferably from about 0° C. to about 80° C. Preferably said film-forming polymer is soluble and/or dispersible in water and/or alcohol. Said film-forming polymer preferably has a molecular weight of at least about 500, more preferably from about 1,000 to about 2,000,000, most preferably from about 5,000 to about 1,000,000.

Some non-limiting examples of homopolymers and copolymers which can be used as the film-forming polymers of the present invention are: adipic acid/dimethylaminohydroxypropyl diethylenetriamine copolymer; adipic acid/epoxypropyl diethylenetriamine copolymer; poly(vinylpyrrolidone/dimethylaminoethyl methacrylate); polyvinyl alcohol; polyvinylpyridine n-oxide; methacryloyl ethyl betaine/methacrylates copolymer; ethyl acrylate/methyl methacrylate/methacrylic acid/acrylic acid copolymer; polyamine resins; and polyquaternary amine resins; poly(ethenylformamide); poly(vinylamine) hydrochloride; poly(vinyl alcohol-co-6% vinylamine); poly(vinyl alcohol-co-12% vinylamine); poly(vinyl alcohol-co-6% vinylamine hydrochloride); and poly(vinyl alcohol-co-12% vinylamine hydrochloride). Preferably, said copolymer and/or homopolymers are selected from the group consisting of adipic acid/dimethylaminohydroxypropyl diethylenetriamine copolymer; poly(vinylpyrrolidone/dimethylaminoethyl methacrylate); polyvinyl alcohol; ethyl acrylate/methyl methacrylate/methacrylic acid/acrylic acid copolymer; methacryloyl ethyl betaine/methacrylates copolymer; polyquaternary amine resins; poly(ethenylformamide); poly(vinylamine) hydrochloride; poly(vinyl alcohol-co-6% vinylamine); poly(vinyl alcohol-co-12% vinylamine); poly(vinyl alcohol-co-6% vinylamine hydrochloride); and poly(vinyl alcohol-co-12% vinylamine hydrochloride).

The film-forming polymer of the present invention is present at least an effective amount to provide shape retention, typically from about 0.1% to about 4.5%, preferably from about 0.2% to about 3%, more preferably from about 0.3% to about 2%, by weight of the composition. Polymer levels higher than about 4.5%, by weight of the composition, are not preferred due to the fact that an undesirable stiffness in the fabric can occur at these higher levels.

III. SILICONE AND FILM-FORMING POLYMER MIXTURE

The wrinkle reducing active of the present invention, in the preferred aspect, comprises a mixture of the silicone and the film-forming polymer which together produce specific filming characteristics on fabric. The filming properties of the wrinkle reducing active on the fabric are measured using Dynamic Mechanical Analysis (DMA) with the Perkin Elmer DMA 7 in tangential fiber extension geometry. Differences found in the Loss Modulus measurement of composition on fabric correlates with the Durable Press Grades (AATCC Method #124), hereinafter "DP grades", for garment appearance after treatment with the compositions of the present invention.

A. Dynamic Mechanical Analysis

Accordingly, in another preferred aspect, the invention comprises using Dynamic Mechanical Analysis, as described hereinafter to identify acceptable active mixtures. A more detailed discussion of Dynamic Mechanical Analysis can be found in "Anelastic and Dielectric Effects in Polymeric Solids," N. G. McCrum, B. E. Read, and G. Williams, incorporated herein by reference.

Using DMA, the rheological properties of compositions can be measured under oscillating load using differing geometries (extensional, parallel, three point bending, and cantilever) and measurement techniques (temperature scan, time scan, frequency scan, creep recovery, and stress scan). The Dynamic Mechanical Analysis method involves applying a fixed volume of liquid sample to a fabric swatch in a tangential fiber extension geometry and monitoring the change in the fabric's ability to dampen the applied stress over time as the sample dries on the surface. DMA measures the Loss Modulus (energy loss) over time as the wet fabric dries. The reported quantity is the Loss Modulus Difference (LMD), the value for the dry fabric minus the value for the wet fabric. It is calculated as an average value over time for the wet and dry fabric portions of the run. Larger values of LMD correlate to higher DP grades for garment appearance. This procedure can be used to determine the operability of many compositions.

B. Filming Characteristics (Loss Modulus Difference)

The Loss Modulus Parameter represents viscous loss, the ability of the sample to adjust to applied stress through energy absorption in the form of molecular rearrangement. Not to be limited by theory, it is believed that as compositions dry on the fabric, they transition from a very low viscosity liquid to a film with both elastic and viscous properties. The compositions' ability to flow, in a molecular sense, influences the properties of the resulting coverage on the fabric fibers. Compositions with a greater Loss Modulus Difference, or ability to flow, provide more flexibility to the fabric therefore, relaxing the wrinkles and maintaining the fiber shape in the fabric.

Specifically, the compositions of the present invention are tested as follows. A 5.3 mm×20 mm swatch of 100% cotton broadcloth is mounted in extensional geometry in a Perkin Elmer DMA 7, available from Perkin Elmer Corp. It is important to keep the swatch centered and square to the geometry. Typically from about 10 microliters to about 25 microliters, preferably from about 15 microliters to about 25 microliters, more preferably from about 20 microliters to about 25 microliters, in three equal aliquots, of a liquid sample of the composition is applied using a microliter pipette in a way so as not to overwet the swatch or cause liquid to run off of the fabric. It is preferable to apply the sample near the upper portion of the swatch and allow it to wick down the swatch. Once the sample is applied, no longer than 2 minutes are allowed to elapse before the run begins. The sample height is read instrumentally; the stress values for analysis are set, 500 mN for static stress, 450 mN for dynamic test, and 110% tension; the furnace is raised; the temperature is allowed to equilibrate; and the run is begun. Typically, the analysis is run at a temperature of from about 20° C. to about 30° C. After the run, the data is smoothed using the Standard Smooth Routine in Change Curvetype® software to calculate the average wet and dry fabric ranges, this software accompanies the Perkin Elmer DMA 7. A table is made of data points in the Select Calc® software, accompanying the Perkin Elmer DMA 7, starting at time 0.0 minutes with 0.7 minute increments. The values corresponding to times 2.8–7.7 minutes are averaged for the wet region, and 25.9–29.4 are averaged for the dry region. LMD is the dry region minus the wet region. Times can vary somewhat with each instrument and calibration, therefore, time are typically averaged over 4 to 5 minutes in the wet region and 4 to 5 minutes in the dry region. Through the above described analysis it is determined that the wrinkle reducing active of the present invention should have a LMD of greater than about $3.3 \times 10^7$ Pascal, preferably from about $3.3 \times 10^7$ Pascal to about $5.5 \times 10^7$ Pascal, more preferably from about $4.0 \times 10^7$ Pascal to about $5.5 \times 10^7$ Pascal, and even more preferably from about $4.7 \times 10^7$ Pascal to about $5.5 \times 10^7$ Pascal in order to work effectively. Wrinkle reducing actives which have a loss modulus difference within these ranges typically show smooth surfaced, web-like, and pliable filming characteristics while wrinkle reducing actives which have a LMD below this range typically exhibit films which are brittle and rough surfaced. The composition of the present invention typically results in a DP grades on the fabric of from about 3.3 to about 4.8, preferably from about 3.5 to about 4.8, more preferably from about 3.8 to about 4.8.

C. Wrinkle Reducing Active

Any silicone and any film-forming polymer can be combined to produce the preferred wrinkle reducing active as long as the combination produces a Loss Modulus Difference within the desired ranges however, some silicone/ polymer combinations are more preferred as the wrinkle reducing active. The wrinkle reducing active is preferably selected from the combinations consisting of aminoethylaminopropyl dimethyl siloxane and adipic acid/ dimethylaminohydroxypropyl diethylenetriamine copolymer; aminoethylaminopropyl dimethyl siloxane, hydroxy terminated dimethyl siloxane (Dimethiconol), and poly(vinylpyrrolidone/dimethylaminoethyl methacrylate); aminoethylaminopropyl dimethyl siloxane, hydroxy terminated dimethyl siloxane (Dimethiconol), and polyquaternary amine resin; hydroxy terminated dimethyl siloxane (Dimethiconol) and methacryloyl ethyl betaine/ methacrylates copolymer; polydimethylsiloxane and ethyl acrylate/methyl methacrylate/methacrylic acid/acrylic acid copolymer; polydimethylsiloxane and adipic acid/ dimethylaminohydroxypropyl diethylenetriamine copolymer; aminoethylaminopropyl dimethyl siloxane and poly(vinylpyrrolidone/dimethylaminoethyl methacrylate); hydroxy terminated dimethyl siloxane (Dimethiconol) and methacryloyl ethyl betaine/methacrylates copolymer; and polydimethylsiloxane and adipic acid/ dimethylaminohydroxypropyl diethylenetriamine copolymer. More preferably said wrinkle reducing active is selected from the combinations consisting of polydimethylsiloxane and adipic acid/dimethylaminohydroxypropyl diethlenetriamine copolymer; and aminoethylaminopropyl dimethyl siloxane, hydroxy terminated dimethyl siloxane (Dimethiconol), and polyquaternary amine resin; even more preferably said wrinkle reducing active is selected from the combination consisting of hydroxy terminated dimethyl siloxane (Dimethiconol) and methacryloyl ethyl betaine/ methacrylates copolymer; and polydimethylsiloxane and ethyl acrylate/methyl methacrylate/methacrylic acid/acrylic acid copolymer; and most preferably said wrinkle reducing active is selected from the combination consisting of aminoethylaminopropyl dimethyl siloxane and adipic acid/ dimethylaminohydroxypropyl diethylenetriamine copolymer; aminoethylaminopropyl dimethyl siloxane, hydroxy terminated dimethyl siloxane, and polyvinyl alcohol; and aminoethylaminopropyl dimethyl siloxane, hydroxy terminated dimethyl siloxane (Dimethiconol) and poly(vinylpyrrolidone/dimethylaminoethyl methacrylate).

Typically the weight ratio of silicone to film-forming polymer is from about 10:1 to about 1:10, preferably from about 5:1 to about 1:5, and more preferably from about 2:1 to about 1:2.

Typically, the preferred wrinkle reducing active is silicone plus film-forming polymer, present at a level of from about 0.1% to about 50%, preferably from about 0.5% to about 10%, more preferably from about 0.5% to about 2%, by weight of the composition.

Concentrated compositions can also be used in order to provide a less expensive product. When a concentrated product is used, i.e., when the wrinkle reducing active is from about 5% to about 50%, by weight of the composition, it is preferable to dilute the composition before treating fabric. Preferably, the wrinkle reducing active is diluted with about 50% to about 10,000%, more preferably from about 50% to about 8,000%, and even more preferably from about 50% to about 5,000%, by weight of the composition, of water.

B. Optional Ingredients

1. Ethoxylated Surfactant

The composition of the present invention can optionally contain an ethoxylated surfactant. When an ethoxylated surfactant is added to the composition of the present invention it is typically added at a level of from about 0.05% to about 3%, preferably from about 0.05% to about 2%, and more preferably from about 0.1% to about 1%, by weight of the composition. Said surfactant is preferably included when the composition is used in a spray dispenser in order to enhance the spray characteristics of the composition and allow the composition to distribute more evenly, and to prevent clogging of the spray apparatus. The ethoxylated surfactant includes compounds having the general formula:

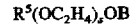

wherein $R^5$ is an alkyl aryl group or an alkyl group having from about 6 to about 18 carbon atoms, preferably from about 8 to about 14, more preferably from about 10 to about 14 carbon atoms; s is an integer from about 3 to about 45, preferably from about 3 to about 20, more preferably from about 5 to about 15; and B is a hydrogen, a carboxylate group, or a sulfate group.

Preferably said ethoxylated surfactant is selected from the group consisting of carboxylated alcohol ethoxylate, also known as ether carboxylate, having a hydrophobic group with from about 12 to about 16 carbon atoms and from about 5 to about 13 ethoxylate groups; alcohol ethoxylate or secondary alcohol ethoxylate having from about 8 to about 20 carbon atoms and from about 4 to about 50 ethoxylate groups; and alkyl phenyl ethoxylate or alkyl aryl ethoxylate having from about 8 to about 10 carbon atoms, preferably from about 14 to 18 carbon atoms and from about 4 to about 50 ethoxylate groups.

Another ethoxylated surfactant suitable for use in the present invention has the formula:

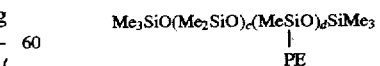

wherein
PE represents —$CH_2CH_2CH_2O(EO)_g(PO)_nZ$;
Me represents methyl;
EO represents ethyleneoxy;
PO represents 1,2-propyleneoxy;

Z can be either a hydrogen or a lower alkyl radical; and c+d+g+h have values which combine to give a molecular weight of from about 600 to about 25,000.

Other ethoxylated surfactants suitable for use in the present invention include ethoxylated quaternary ammonium surfactants. Some preferred ethoxylated quaternary ammonium surfactants include PEG-5 cocomonium methosulfate; PEG-15 cocomonium chloride; PEG-15 oleammonium chloride; and bis(polyethoxyethanol)tallow ammonium chloride.

2. Soil Release Polymers

In the present invention, an optional soil release agent can be added. The wrinkle reducing composition of the present invention herein can contain from about 0% to about 5%, preferably from about 0.05% to about 3%, more preferably from about 0.1% to about 2%, by weight of the composition, of soil release agent. Polymeric soil release agents useful in the present invention include copolymeric blocks of terephthalate and polethylene oxide or polypropylene oxide, and the like.

A preferred soil release agent is a copolymer having blocks of terephthalate and polyethylene oxide. More specifically, these polymers are comprised of repeating units of ethylene terephthalate and polyethylene oxide terephthalate at a molar ratio of ethylene terephthalate units to polyethylene oxide terephthalate units of from about 25:75 to about 35:65, said polyethylene oxide terephthalate containing polyethylene oxide blocks having molecular weights of from about 300 to about 2000. The molecular weight of this polymeric soil release agent is in the range of from about 5,000 to about 55,000.

Another preferred polymeric soil release agent is a crystallizable polyester with repeat units of ethylene terephthalate units containing from about 10% to about 15% by weight of ethylene terephthalate units together with from about 10% to about 50% by weight of polyoxyethylene terephthalate units, derived from a polyoxyethylene glycol of average molecular weight of from about 300 to about 6,000, and the molar ratio of ethylene terephthalate units to polyoxyethylene terephthalate units in the crystallizable polymeric compound is between 2:1 and 6:1. Examples of this polymer include the commercially available materials Zelcon 4780® (from Dupont) and Milease T® (from ICI).

Highly preferred soil release agents are polymers of the generic formula:

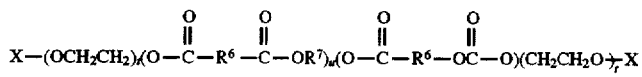

in which each X can be a suitable capping group, with each X typically being selected from the group consisting of H, and alkyl or acyl groups containing from about 1 to about 4 carbon atoms. each t is selected for water solubility and generally is from about 6 to about 113, preferably from about 20 to about 50. u is critical to formulation in a liquid composition having a relatively high ionic strength. There should be very little material in which u is greater than 10. Furthermore, there should be at least 20%, preferably at least 40%, of material in which u ranges from about 3 to about 5.

The $R^6$ moieties are essentially 1,4-phenylene moieties. As used herein, the term "the $R^6$ moieties are essentially 1,4-phenylene moieties" refers to compounds where the $R^6$ moieties consist entirely of 1,4-phenylene moieties, or are partially substituted with other arylene or alkarylene moieties, alkylene moieties, alkenylene moieties, or mixtures thereof. Arylene and alkarylene moieties which can be partially substituted for 1,4-phenylene include 1,3-phenylene, 1,2-phenylene, 1,8-naphthylene, 1,4-naphthylene, 2,2-biphenylene, 4,4-biphenylene, and mixtures thereof. Alkylene and alkenylene moieties which can be partially substituted include 1,2-propylene, 1,4-butylene, 1,5-pentylene, 1,6-hexamethylene, 1,7-heptamethylene, 1,8-octamethylene, 1,4-cyclohexylene, and mixtures thereof.

For the $R^6$ moieties, the degree of partial substitution with moieties other than 1,4-phenylene should be such that the soil release properties of the compound are not adversely affected to any great extent. Generally the degree of partial substitution which can be tolerated will depend upon the backbone length of the compound, i.e., longer backbones can have greater partial substitution for 1,4-phylene moieties. Usually, compounds where the $R^6$ comprise from about 50% to about 100% 1,4-phenylene moieties (from 0% to about 50% moieties other than 1,4-phenylene) have adequate soil release activity. For example, polyesters made according to the present invention with a 40:60 mole ratio of isophthalic (1,3-phenylene) to terephthalic (1,4-phenylene) acid have adequate soil release activity. However, because most polyesters used in fiber making comprise ethylene terephthalate units, it is usually desirable to minimize the degree of partial substitution with moieties other than 1,4-phenylene for best soil release activity. Preferably, the $R^6$ moieties consist entirely of (i.e., comprise 100%) 1,4-phenylene moieties, i.e., each $R^6$ moiety is 1,4-phenylene.

For the $R^7$ moieties, suitable ethylene or substituted ethylene moieties include ethylene, 1,2-propylene, 1,2-butylene, 1,2-hexylene, 3-methoxy-1,2-propylene, and mixtures thereof. Preferably, the $R^7$ moieties are essentially ethylene moieties, 1,2-propylene moieties, or mixtures thereof. Inclusion of a greater percentage of ethylene moieties tends to improve the soil release activity of compounds. Surprisingly, inclusion of a greater percentage of 1,2-propylene moieties tends to improve the water solubility of compounds.

Therefore, the use of 1,2-propylene moieties or a similar branched equivalent is desirable for incorporation of any substantial part of the soil release component in the liquid fabric softener compositions. Preferably, from about 75% to about 100%, are 1,2-propylene moieties.

A more complete disclosure of soil release agents is contained in U.S. Pat. Nos. 4,661,267, Decker, Konig, Straathof, and Gosselink, issued Apr. 28, 1987; 4,711,730, Gosselink and Diehl, issued Dec. 8, 1987; 4,749,596, Evans, Huntington, Stewart, Wolf, and Zimmerer, issued Jun. 7, 1988; 4,818,569, Trinh, Gosselink, and Rattinger, issued Apr. 4, 1989; 4,877,896, Maldonado, Trinh, and Gosselink, issued Oct. 31, 1989; 4,956,447, Gosselink et al., issues Sep. 11, 1990; and 4,976,879, Maldonado, Trinh, and Gosselink, issued Dec. 11, 1990, all of said patents being incorporated herein by reference.

3. Antistatic Agents

The composition of the present invention can optionally include antistatic agents. When said antistatic agents are present in the composition they are present at a level of from about 0% to about 5%, preferably from about 0.005% to about 5%, more preferably from about 0.05% to about 2%, and most preferably from about 0.2% to about 1%, by weight of the composition. Preferred antistatic agents of the present invention are cationic surfactants, preferably quaternary ammonium salts having the general formulas:

$$[R^8N^+R_3^9]X^- \text{ or}$$

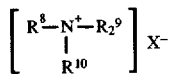

wherein the $R^8$ group is a $C_{10}$–$C_{22}$ hydrocarbon group, preferably a $C_{12}$–$C_{18}$ alkyl group or the corresponding ester linkage interrupted group with a short alkylene ($C_1$–$C_4$) group between the ester linkage and the N, and having a similar terminal hydrocarbon group, .g., a fatty acid ester of choline, preferably $C_{12}$–$C_{14}$ (coco) choline ester and/or $C_{16}$–$C_{18}$ tallow choline ester. Each $R^9$ is a $C_1$–$C_4$ alkyl or substituted (e.g., hydroxy) alkyl, or hydrogen, preferably methyl; each $R^{10}$ is a benzyl group; and the counterion $X^-$ is a softener compatible anion, for example, chloride, bromide, methyl sulfate, etc. Some preferred quaternary ammonium compounds include alkyl benzyl dimethyl ammonium chloride; dicoco quaternary ammonium chloride; coco dimethyl benzyl ammonium chloride; soya trimethyl quaternary ammonium chloride; hydrogenated tallow dimethyl benzyl ammonium chloride; and methyl dihydrogenated tallow benzyl ammonium chloride.

Other preferred antistatic agents of the present invention are alkyl imidazolinium salts having the general formula:

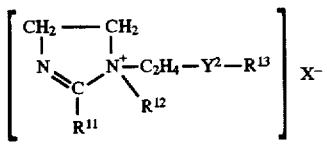

wherein $Y^2$ is —C(O)—O—, —O—(O)—C—, —C(O)—N($R^{14}$), or —N($R^{14}$)—C(O)— in which $R^{14}$ is hydrogen or a $C_1$–$C_4$ alkyl radical; $R^{11}$ and $R^{13}$ are each independently selected from $R^8$ and $R^9$ as defined hereinbefore for the cationic surfactant, with only one being $R^8$; and each $R^{12}$ is a $C_1$–$C_4$ alkyl radical.

Other suitable antistatic agents are the ion pairs of, e.g., anionic detergent surfactants and fatty amines, or quaternary ammonium derivatives thereof, e.g., those disclosed in U.S. Pat. No. 4,756,850, Nayar, issued Jul. 12, 1988, said patent being incorporated herein by reference. The ion pair complexes can be represented by the following formula:

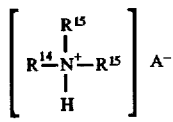

wherein each $R^{14}$ can independently be $C_{12}$–$C_{20}$ alkyl or alkenyl, and $R^{15}$ is H or $CH_3$. $A^-$ represents an anionic compound and includes a variety of anionic surfactants, as well as related shorter alkyl chain compounds which need not exhibit surface activity. $A^-$ is selected from the group consisting of alkyl sulfonates, aryl sulfonates, alkylaryl sulfonates, alkyl sulfates, dialkyl sulfosuccinates, alkyl oxybenzene sulfonates, acyl isethionates, acylalkyl taurates, alkyl ethoxylates sulfates, olefin sulfates, preferably benzene sulfonates, and $C_1$–$C_5$ linear alkyl benzene sulfonates, or mixtures thereof.

Other suitable antistatic agents are ethoxylated and/or propylated sugar derivatives. Said sugar derivatives have an empirical formula as follows:

$$R^{16}{}_z\text{-(sugar)}(R^{17}O)_wC$$

wherein $R^{16}$ is a hydrophobic group containing from about 8 to about 30, preferably from about 12 to about 22, more preferably from about 16 to about 18 carbon atoms; "sugar" refers to a polyhydroxy group, preferably derived from sugar, sugar alcohol, or similar polyhydroxy compound; $R^{17}$ is an alkylene group, preferably ethylene or propylene, more preferably ethylene; z is a number from 1 to about 4, preferably 2; and w is a number from about 5 to about 100, preferably from about 10 to about 40. A preferred compound of this type is polyethoxylated sorbitan monostearate, e.g., Glycosperse S-20® from Lonza, which contains about 20 ethoxylate moieties per molecule.

4. Other Optional Ingredients

The present invention can include optional components conventionally used in textile treatment compositions, for example, colorants, perfumes, preservatives, bactericides, optical brighteners, opacifiers, surfactants, anti-shrinkage agents, germicides, fungicides, anti-oxidants, and the like. The compositions are preferably free of any material that would soil or stain fabric, and are also substantially free of starch. Typically, there should be less than about 0.5%, by weight of the composition, preferably less than about 0.3%, more preferably less than about 0.1%, by weight of the composition, of starch and/or modified starch.

C. Liquid Carrier

The liquid carrier used in the composition of the present invention is preferably an aqueous system comprising water. Optionally, but not preferably, in addition to the water, the carrier can contain a low molecular weight organic solvent that is highly soluble in water, e.g., $C_1$–$C_4$ monohydric alcohols, $C_2$–$C_6$ polyhydric alcohols, such as alkylene glycols, polyalkylene glycols, etc., alkylene carbonates, and mixtures thereof. Examples of these water-soluble solvents include ethanol, propanol, isopropanol, etc. Water is a preferred liquid carrier due to its low cost, availability, safety, and environmental compatibility. Water can be distilled, deionized, or tap water.

The level of liquid carrier in the compositions of the present invention is typically greater than about 80%, preferably greater than about 90%, more preferably greater than about 95%, by weight of the composition. When a concentrated composition is used, the level of liquid carrier is typically from about 50% to about 95%, by weight of the composition, preferably from about 60% to about 93%, more preferably from about 60% to about 85%, by weight of the composition.

D. Packaging

In another aspect of the invention, an article of manufacture is provided that comprises an article of manufacture comprising a wrinkle reducing composition comprising a wrinkle reducing active selected from the group consisting of an effective amount of silicone, an effective amount of film-forming polymer and mixtures thereof, and a liquid carrier, and a spray dispensing device.

The dilute compositions, i.e., compositions containing from about 0.1% to about 5%, by weight of the composition, of wrinkle reducing active, of the present invention are preferably sprayed onto fabrics and therefore are typically packaged in a spray dispenser. The spray dispenser can be any of the manually activated means for producing a spray of liquid droplets as is known in the art, e.g. trigger-type, pump-type, non-aerosol self-pressurized, and aerosol-type spray means. It is preferred that at least about 70%, more preferably, at least about 80%, most preferably at least about 90% of the droplets have a particle size of smaller than about 200 microns.

The spray dispenser can be an aerosol dispenser. Said aerosol dispenser comprises a container which can be constructed of any of the conventional materials employed in fabricating aerosol containers. The dispenser must be capable of withstanding internal pressure in the range of from about 20 to about 110 p.s.i.g., more preferably from about 20 to about 70 p.s.i.g. The one important requirement concerning the dispenser is that it be provided with a valve member which will permit the wrinkle reducing composition contained in the dispenser to be dispensed in the form of a spray of very fine, or finely divided, particles or droplets. The aerosol dispenser utilizes a pressurized sealed container from which the wrinkle reducing composition is dispensed through a special actuator/valve assembly under pressure. The aerosol dispenser is pressurized by incorporating therein a gaseous component generally known as a propellant. Common aerosol propellants, e.g., gaseous hydrocarbons such as isobutane, and mixed halogenated hydrocarbons, are not preferred. Halogenated hydrocarbon propellants such as chlorofluoro hydrocarbons have been alleged to contribute to environmental problems. Preferred propellants are compressed air, nitrogen, inert gases, carbon dioxide, etc. A more complete description of commercially available aerosol-spray dispensers appears in U.S. Pat. Nos. 3,436,772, Stebbins, issued Apr. 8, 1969; and 3,600,325, Kaufinan et al., issued Aug. 17, 1971; both of said references are incorporated herein by reference.

Preferably the spray dispenser can be a self-pressurized non-aerosol container having a convoluted liner and an elastomeric sleeve. Said self-pressurized dispenser comprises a liner/sleeve assembly containing a thin, flexible radially expandable convoluted plastic liner of from about 0.010 to about 0.020 inch thick, inside an essentially cylindrical elastomeric sleeve. The liner/sleeve is capable of holding a substantial quantity of odor-absorbing fluid product and of causing said product to be dispensed. A more complete description of self-pressurized spray dispensers can be found in U.S. Pat. Nos. 5,111,971, Winer, issued May 12, 1992, and 5,232,126, Winer, issued Aug. 3, 1993; both of said references are herein incorporated by reference. Another type of aerosol spray dispenser is one wherein a barrier separates the wrinkle reducing composition from the propellant (preferably compressed air or nitrogen), as is disclosed in U.S. Pat. No. 4,260,110, issued Apr. 7, 1981, incorporated herein by reference. Such a dispenser is available from EP Spray Systems, East Hanover, N.J.

More preferably, the spray dispenser is a non-aerosol, manually activated, pump-spray dispenser. Said pump-spray dispenser comprises a container and a pump mechanism which securely screws or snaps onto the container. The container comprises a vessel for containing the wrinkle reducing composition to be dispensed.

The pump mechanism comprises a pump chamber of substantially fixed volume, having an opening at the inner end thereof. Within the pump chamber is located a pump stem having a piston on the end thereof disposed for reciprocal motion in the pump chamber. The pump stem has a passageway there through with a dispensing outlet at the outer end of the passageway and an axial inlet port located inwardly thereof.

The container and the pump mechanism can be constructed of any conventional material employed in fabricating pump-spray dispensers, including, but not limited to: polyethylene; polypropylene; polyethyleneterephthalate; blends of polyethylene, vinyl acetate, and rubber elastomer. Other materials can include stainless steel. A more complete disclosure of commercially available dispensing devices appears in: U.S. Pat. Nos. 4,895,279, Schultz, issued Jan. 23, 1990; 4,735,347, Schultz et al., issued Apr. 5, 1988; and 4,274,560, Carter, issued Jun. 23, 1981; all of said references are herein incorporated by reference.

Most preferably, the spray dispenser is a manually activated trigger-spray dispenser. Said trigger-spray dispenser comprises a container and a trigger both of which can be constructed of any of the conventional material employed in fabricating trigger-spray dispensers, including, but not limited to: polyethylene; polypropylene; polyacetal; polycarbonate; polyethyleneterephthalate; polyvinyl chloride; polystyrene; blends of polyethylene, vinyl acetate, and rubber elastomer. Other materials can include stainless steel and glass. The trigger-spray dispenser does not incorporate a propellant gas. The trigger-spray dispenser herein is typically one which acts upon a discrete amount of the wrinkle reducing composition itself, typically by means of a piston or a collapsing bellows that displaces the composition through a nozzle to create a spray of thin liquid. Said trigger-spray dispenser typically comprises a pump chamber having either a piston or bellows which is movable through a limited stroke response to the trigger for varying the volume of said pump chamber. This pump chamber or bellows chamber collects and holds the product for dispensing. The trigger spray dispenser typically has an outlet check valve for blocking communication and flow of fluid through the nozzle and is responsive to the pressure inside the chamber. For the piston type trigger sprayers, as the trigger is compressed, it acts on the fluid in the chamber and the spring, increasing the pressure on the fluid. For the bellows spray dispenser, as the bellows is compressed, the pressure increases on the fluid. The increase in fluid pressure in either trigger spray dispenser acts to open the top outlet check valve. The top valve allows the product to be forced through the swirl chamber and out the nozzle to form a discharge pattern. An adjustable nozzle cap can be used to vary the pattern of the fluid dispensed.

For the piston spray dispenser, as the trigger is released, the spring acts on the piston to return it to its original position. For the bellows spray dispenser, the bellows acts as the spring to return to its original position. This action causes a vacuum in the chamber. The responding fluid acts to close the outlet valve while opening the inlet valve drawing product up to the chamber from the reservoir.

A more complete disclosure of commercially available dispensing devices appears in U.S. Pat. Nos. 4,082,223, Nozawa, issued Apr. 4, 1978; 4,161,288, McKinney, issued Jul. 17, 1985; 4,434,917, Saito et al., issued Mar. 6, 1984; and 4,819,835, Tasaki, issued Apr. 11, 1989; 5,303,867, Peterson, issued Apr. 19, 1994; all of said references are incorporated herein by reference.

A broad array of trigger sprayers or finger pump sprayers are suitable for use with the compositions of this invention. These are readily available from suppliers such as Calmar, Inc., City of Industry, Calif.; CSI (Continental Sprayers, Inc.), St. Peters, Mo.; Berry Plastics Corp., Evansville, Ind.—a distributor of Guala® sprayers; or Seaquest Dispensing, Cary, Ill.

The preferred trigger sprayers are the blue inserted Guala® sprayer, available from Berry Plastics Corp., the Calmar TS800-1A® sprayers, available from Calmar Inc., or the CSI T7500® available from Continental Sprayers, Inc., because of the fine uniform spray characteristics, spray volume, and pattern size. Any suitable bottle or container can be used with the trigger sprayer, the preferred bottle is a 17 fl-oz. bottle (about 500 ml) of good ergonomics similar in shape to the Cinch® bottle. It can be made of any materials such as high density polyethylene, polypropylene, polyvinyl chloride, polystyrene, polyethylene terephthalate, glass, or any other material that forms bottles. Preferably, it is made of high density polyethylene or polyethylene terephthalate.

For smaller four fl-oz. size (about 118 ml), a finger pump can be used with canister or cylindrical bottle. The preferred pump for this application is the cylindrical Euromist II® from Seaquest Dispensing.

All percentages, ratios, and parts herein, in the Specification, Examples, and Claims, are by weight and are approximations unless otherwise stated.

E. METHOD OF USE

An effective amount of the composition of the present invention is preferably sprayed onto fabrics, particularly clothing. When the composition is sprayed onto fabric an effective amount should be deposited onto the fabric without causing saturation of the fabric, typically from about 10% to about 85%, preferably from about 15% to about 65%, more preferably from about 20% to about 50%, by weight of the fabric. The amount of active typically sprayed onto the fabric is from about 0.1% to about 4%, preferably from about 0.2% to about 3%, more preferably from about 0.3% to about 2%, by weight of the fabric. Once an effective amount of the composition is sprayed onto the fabric the fabric is optionally, but preferably stretched. The fabric is typically stretched perpendicular to the wrinkle. The fabric can also be smoothed by hand after it has been sprayed. The smoothing movement works particularly well on areas of clothing that have interface sewn into them, or on the hem of clothing. Once the fabric has been sprayed and optionally, but preferably, stretched, it is hung until dry.

The composition of the present invention can also be used as an ironing aid. An effective amount of the composition can be sprayed onto fabric, wherein said fabric should not be sprayed to saturation. The fabric can be ironed at the normal temperature at which it should be ironed. The fabric can be sprayed with an effective amount of the composition, allowed to dry and then ironed, or sprayed and ironed immediately.

The following are non-limiting examples of the instant compositions.

| Material | % Activity | A | B | C | D | E |
| --- | --- | --- | --- | --- | --- | --- |
| DC 108 ®[1] | 35 | 1.05 | — | 0.53 | — | 0.53 |
| DC 1669 ®[2] | 35 | — | — | 0.53 | 1.05 | 0.53 |
| GE SM2140[3] ® | 50 | — | 1.00 | — | — | — |
| Copolymer 958 ®[4] | 50 | — | — | 0.50 | — | — |
| Cartaretin F-23 ®[5] | 23 | 0.46 | — | — | — | — |
| Amerhold DR-25 ®[6] | 25 | — | 0.50 | — | — | — |
| Diaformer Z-SM[7] ® | 30 | — | — | — | 0.50 | — |
| Kymene 557H[8] ® | 12.5 | — | — | — | — | 0.50 |
| Sandopan DTC[9] ® | 90 | 0.30 | 0.10 | 0.10 | 0.10 | 0.10 |
| Perfume | 100 | 0.01 | 0.01 | 0.01 | 0.01 | 0.01 |
| Preservative | 1.5 | 0.0003 | 0.0003 | 0.0003 | 0.0003 | 0.0003 |
| DI Water | 100 | Balance | Balance | Balance | Balance | Balance |

| | % Activity | F | G | H | I | J |
| --- | --- | --- | --- | --- | --- | --- |
| DC 108 ® | 35 | — | — | — | — | 0.53 |
| DC 1669 ® | 35 | — | — | — | — | 0.53 |
| GE SM2140 ® | 50 | — | 1.00 | — | — | — |
| Sandoperm ME ®[10] | 20 | — | — | 0.80 | — | — |
| DC 1784 ®[11] | 35 | — | — | — | 1.20 | — |
| GE SM2068A ®[12] | 35 | 1.05 | — | — | — | — |
| Cartaretin F-23 ® | 23 | 0.46 | 0.46 | — | — | — |
| Copolymer 937 ®[13] | 20 | — | — | 0.65 | — | — |
| Vinex 2019 ®[14] | 12.5 | — | — | — | — | 0.50 |
| Diaformer Z-SM ® | 30 | — | — | — | 0.80 | — |
| Silwet L7607[15] | 100 | — | 0.10 | — | — | — |
| Neodol 23-6.5 ®[16] | 100 | — | — | 0.20 | 0.10 | 0.10 |
| Sandopan DTC ® | 90 | 0.30 | — | — | — | 0.10 |
| Perfume | 100 | 0.015 | 0.015 | 0.015 | 0.015 | 0.01 |
| Preservative | 1.5 | 0.0003 | 0.0003 | 0.0003 | 0.0003 | 0.0003 |
| DI Water | 100 | Balance | Balance | Balance | Balance | Balance |

[1] Aminoethylaminopropyl dimethyl siloxane (viscosity of about 100,000 cst)
[2] Hydroxy terminated dimethyl siloxane also known as Dimethiconol (viscosity of about 1,000 cst)
[3] Polydimethylsiloxane (viscosity of about 10,000 cst)
[4] Poly(vinylpyrrolidone/dimethylaminoethyl methacrylate) MW about 100,000
[5] Adipic acid/dimethylaminohydroxypropyl diethylenetriamine copolymer
[6] Ethyl acrylate/methyl methacrylate/methacrylic acid/acrylic acid copolymer
[7] Methacryloyl ethyl betaine/methacrylates copolymer
[8] Polyquaternary amine resins
[9] Trideceth-7 Carboxylic acid
[10] Aminoethylaminopropyl dimethyl siloxane

[11] Hydroxy terminated dimethyl siloxane also known as Dimethiconol (viscosity of about 1,000,000 cst)
[12] Polydimethylsiloxane (viscosity of about 1,000,000 cst)
[13] Poly(vinylpyrrolidone/dimethylaminoethyl methacrylate) (molecular weight of about 1,000,000)
[14] Polyvinyl alcohol copolymer resin
[15] Polyethylene oxide modified polydimethylsiloxane
[16] $C_{12}$-$C_{13}$ alkylpolyethoxylate (7)

| FORMULA | DP GRADE |
|---|---|
| A | 4.5 |
| B | 4.2 |
| C | 4.6 |
| D | 4.0 |
| E | 3.8 |
| F | 3.5 |
| J | 4.0 |

Preparation of Example I

The ethoxylated surfactant is added to the deionized water at about 21° C. to about 27° C. with stirring. The film-forming polymer is added to the water/surfactant mixture and stirring is continued. The silicone is added to the mixture with a low amount of agitation to form a homogenous mixture. The perfume and antimicrobial are added. The mixture is stirred for about 3 to about 5 minutes with low agitation.

| Material Wt. % | % Active | K Wt. % | L Wt. % | M Wt. % | N Wt. % | O Wt. % | P Wt. % | Q Wt. % |
|---|---|---|---|---|---|---|---|---|
| DC 108 ® | 35 | 1.0 | 0.5 | 0.5 | — | 0.5 | — | 1.0 |
| DC 1669 ® | 35 | — | 0.5 | 0.5 | — | 0.5 | — | — |
| Softener DSW ®[17] | 40 | — | — | — | 1.0 | — | — | — |
| Sandoperm ME ® | 20 | — | — | — | — | — | 1.0 | — |
| Carteretin F-23 ® | 23 | 0.5 | — | — | — | — | — | — |
| Copolymer 958 ® | 50 | — | 0.5 | — | — | — | 0.5 | — |
| Vinex 2019 ® | 12.5 | — | — | 0.5 | — | — | — | — |
| Delsette 101 ®[18] | 12.5 | — | — | — | 0.5 | — | — | — |
| Cypro 515 ®[19] | 50 | — | — | — | — | 0.5 | — | — |
| Copolymer 937 ® | 20 | — | — | — | — | — | — | 0.65 |
| Sandopan DTC ® | 90 | 0.3 | 0.1 | 0.1 | 0.1 | 0.1 | 0.1 | 0.2 |
| Perfume | 100 | 100 | 0.015 | 0.015 | 0.015 | 0.015 | 0.015 | 0.015 |
| Preservative | 1.5 | 1.5 | 0.0003 | 0.0003 | 0.0003 | 0.0003 | 0.0003 | 0.0003 |
| DI Water | | | Balance | Balance | Balance | Balance | Balance | Balance |

[17] epoxyfunctionaldimethylsiloxane
[18] adipic acid/epoxypropyl diethylenetriamine copolymer
[19] polyamine resins

| Formula | Loss Modulus Difference ($\times 10^7$ Pa) | Durable Press Grade |
|---|---|---|
| K | 5.31 | 4.5 |
| L | 5.01 | 4.3 |
| M | 4.76 | 4.0 |
| N | 4.37 | 3.5 |
| O | 4.17 | 3.5 |
| P | 3.26 | 3.3 |
| Q | 3.31 | 3.3 |
| R[20] | 2.48 | 2.1 |

[20] Magic Sizing ® Spray containing Sodium Carboxymethyl Cellulose; Polyethylene Glycol; Silicone; Water and (minors)

Preparation of Example II

The compositions are prepared as in Example I. The Loss Modulus Difference is determined by applying fixed volume of liquid sample to a fabric swatch, i.e. 100% cotton broadcloth, in a tangential fiber extension geometry and monitoring the change in the fabric's ability to dampen the applied stress over time as the sample dries on the surface. Measurements are made isothermally at from about 20° C. to about 30° C., e.g., room temperature. Loss Modulus, or energy loss, is measured as the fabric dries and is reported as the Loss Modulus Difference (LMD) between the dry fabric at the end of the run and the wet fabric at the beginning of the run.

An effective amount of the above compositions are placed in a CSI T7500® sprayer and the sprayer is used to treat wrinkled fabrics.

The actives in compositions having a Loss Modulus Difference of from about $3.3 \times 10^7$ Pascals to about $5.5 \times 10^7$ Pascals are selected as having acceptable wrinkle reducing properties.

What is claimed is:

1. An article of manufacture, which comprises:
   a wrinkle reducing active composition, comprising:
   1. a wrinkle reducing active, comprising:
      a. from about 0.1% to about 4.5%, by weight of the composition, silicone;
      b. from about 0.1% to about 4.5%, by weight of the composition, film-forming polymer having a glass transition temperature of from about −20° C. to about 150° C.; and
   2. a liquid carrier; and said wrinkle reducing active composition being packaged in
   a spray dispenser, for spraying said wrinkle reducing composition onto fabric, wherein said spray dispenser is capable of dispensing onto said fabric an amount of said wrinkle reducing active of from about 0.1% to about 4%, by weight of said fabric; and wherein said wrinkle reducing active is substantially free of starch, modified starch, and mixtures thereof; and wherein said wrinkle reducing composition results in a Loss Modulus Difference of greater than about $3.3 \times 10^7$ Pascal on fabric to provide acceptable wrinkle reducing properties.

2. The article of manufacture of claim 1 wherein said silicone is present at a level of from about 0.2% to about 4%, by weight of the composition.

3. The article of manufacture of claim 2 wherein said silicone is present at a level of from about 0.3% to about 2%, by weight of the composition.

4. The article of manufacture of claim 1 wherein said silicone is selected from the group consisting of polydimethylsiloxane gums and fluids, aminosilicones, reactive silicones and phenylsilicones.

5. The article of manufacture of claim 4 wherein said silicone is selected from the group consisting of A. polyalkyl or polyaryl silicones with the following structure:

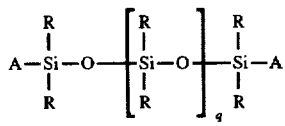

wherein each R is a phenyl, a hydroxy, an alkyl an aryl, or mixtures thereof; q is an integer from about 7 to about 8,000; and each A is hydrogen, methyl, methoxy, ethoxy, hydroxy, propoxy, aryloxy, or mixtures thereof;

B. silicone materials having the formula:

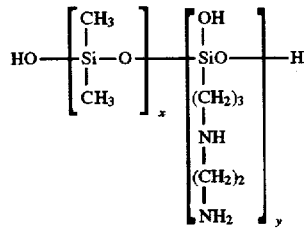

wherein x and y are integers which depend on the molecular weight of the silicone and wherein said silicone has a viscosity of from about 10,000 centistokes to about 500,000 centistokes at 25° C.; and C. mixtures thereof.

6. The article of manufacture of claim 1 wherein said film-forming polymer is present at a level of from about 0.2% to about 3%, by weight of the composition.

7. The article of manufacture of claim 6 wherein said film-forming polymer is present at a level of from about 0.3% to about 2%, by weight of the composition.

8. The article of manufacture of claim 1 wherein said film-forming polymer is comprised of monomers selected from the group consisting of adipic acid; ethenyl formamide; diethylene triamine; vinyl amine; acrylic acid; methacrylic acid; N,N-dimethylacrylamide; N-t-butyl acrylamide; maleic acid; maleic anhydride, and its half esters; crotonic acid; itaconic acid; acrylamide; acrylate alcohols; hydroxyethyl methacrylate; vinyl pyrrolidone; vinyl ethers; maleimides; vinyl pyridine; vinyl imidazole and other polar vinyl heterocyclics; styrene sulfonate; allyl alcohol; vinyl alcohol; vinyl caprolactam; acrylic or methacrylic acid esters of $C_1$–$C_{18}$ alcohols; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; methoxy ethyl methacrylate; and mixtures thereof.

9. The article of manufacture of claim 8 wherein said film-forming polymers and film-forming polymers are selected from the group consisting of adipic acid/ dimethylaminohydroxypropyl diethylenetriamine copolymer; adipic acid/epoxypropyl diethylenetriamine copolymer; poly(vinylpyrrolidone/dimethylaminoethyl methacrylate); polyvinyl alcohol; polyvinylpyridine n-oxide; methacryloyl ethyl betaine/methacrylates copolymer; ethyl acrylate/methyl methacrylate/methacrylic acid/ acrylic acid copolymer; polyamine resins; polyquaternary amine resins; poly(ethyleneformamide); poly(vinylamine) hydrochloride; poly(vinyl alcohol-co-vinylamine); poly (vinyl alcohol-co-6% vinylamine); poly(vinyl alcohol-co-12% vinylamine); poly(vinyl alcohol-co-6% vinylamine hydrochloride); and poly(vinyl alcohol-co-12% vinylamine hydrochloride).

10. The article of manufacture of claim 1 wherein said film-forming polymer has a glass transition temperature of from about −10° C. to about 150° C.

11. The article of manufacture of claim 9 wherein said film-forming polymer has a glass transition temperature of from about 0° C. to about 80° C., and wherein said film-forming polymer is soluble, dispersible, or both in water, alcohol, or mixtures thereof, and wherein said film-forming polymer has a molecular weight of at least about 500.

12. The article of manufacture of claim 1 wherein said wrinkle reducing composition is a mixture of silicone and film-forming polymer having a weight ratio of silicone to polymer of from about 10:1 to about 1:10.

13. The article of manufacture of claim 10 wherein weight ratio is from about 5:1 to about 1:5.

14. The article of manufacture of claim 13 wherein weight ratio is from about 2:1 to about 1:2.

15. The article of manufacture of claim 12 wherein said silicone is selected from the group consisting of polydimethylsiloxane gums and fluids, aminosilicones, reactive silicones and phenylsilicones.

16. The article of manufacture of claim 14 wherein said silicone is selected from the group consisting of A. polyalkyl or polyaryl silicones with the following structure:

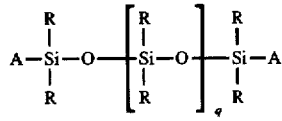

wherein each R is a phenyl, a hydroxy, an alkyl an aryl, or mixtures thereof; q is an integer from about 7 to about 8,000; and each A is hydrogen, methyl, methoxy, ethoxy, hydroxy, propoxy, aryloxy, or mixtures thereof;

B. silicone materials having the formula:

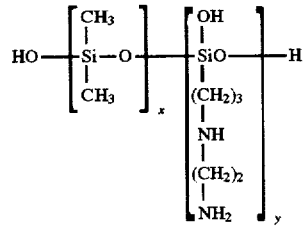

wherein x and y are integers which depend on the molecular weight of the silicone and wherein said silicone has a viscosity of from about 10,000 centistokes to about 500,000 centistokes at 25° C.; and C. mixtures thereof.

17. The article of manufacture of claim 14 wherein said film-forming polymer is comprised of monomers selected from the group consisting of adipic acid; ethenyl formamide; diethylene triamine; vinyl amine; acrylic acid; methacrylic acid; N,N-dimethylacrylamide; N-t-butyl acrylamide; maleic acid; maleic anhydride, and its half esters; crotonic acid; itaconic acid; acrylamide; acrylate alcohols; hydroxyethyl methacrylate; vinyl pyrrolidone; vinyl ethers; maleimides; vinyl pyridine; vinyl imidazole and other polar vinyl heterocyclics; styrene sulfonate; allyl alcohol; vinyl alcohol; vinyl caprolactam; acrylic or methacrylic acid esters of $C_1$–$C_{18}$ alcohols; polystyrene macromer; vinyl acetate; vinyl chloride; vinylidene chloride; vinyl propionate; alphamethylstyrene; t-butylstyrene; butadiene; cyclohexadiene; ethylene; propylene; vinyl toluene; methoxy ethyl methacrylate; and mixtures thereof.

18. The article of manufacture of claim 15 wherein said film-forming polymers are selected from the group consisting of adipic acid/dimethylaminohydroxypropyl diethylenetriamine copolymer; adipic acid/epoxypropyl diethylenetriamine copolymer; poly(vinylpyrrolidone/dimethylaminoethyl methacrylate); polyvinyl alcohol; polyvinylpyridine n-oxide; methacryloyl ethyl betaine/methacrylates copolymer; ethyl acrylate/methyl methacrylate/methacrylic acid/acrylic acid copolymer; polyamine resins; polyquaternary amine resins; poly(ethyleneformamide); poly(vinylamine) hydrochloride; poly(vinyl alcohol-co-vinylamine); poly(vinyl alcohol-co-6% vinylamnine); poly(vinyl alcohol-co-12% vinylamine); poly(vinyl alcohol-co-6% vinylamine hydrochloride); and poly(vinyl alcohol-co-12% vinylamine hydrochloride).

19. The article of manufacture of claim 16 wherein said film-forming polymer has a glass transition temperature of from about of from about −20° C. to about 150° C.

20. The article of manufacture of claim 1 wherein said liquid carrier is water.

21. The article of manufacture of claim 1 wherein said spray dispenser is selected from the group consisting of aerosol spray dispensers; self-pressurized, non-aerosol spray dispensers; pump-spray dispensers; and trigger-spray dispensers.

22. The article of manufacture of claim 19 wherein said spray dispenser is a pump-spray dispenser.

23. The article of manufacture of claim 19 wherein said spray dispenser is a trigger-spray dispenser.

24. The article of manufacture of claim 1 wherein said wrinkle reducing composition further comprises an ethoxylated surfactant.

25. The article of manufacture of claim 1 wherein said wrinkle reducing composition further comprises a soil release polymer.

26. The article of manufacture of claim 1 wherein said wrinkle reducing composition further comprises an antistatic agent.

27. The article of manufacture of claim 25 wherein said silicone is present at a level of from about 0.1% to about 4.5%, by weight of the composition.

28. An article of manufacture, which comprises:
  a wrinkle reducing composition, comprising:
   1. silicone selected from the group consisting of polydimethylsiloxane gums and fluids, aminosilicones, reactive silicones and phenylsilicones
   2. ethoxylated surfactant;
   3. antistatic agent; and
   4. water; and said wrinkle reducing active composition being packaged in
  a trigger-spray dispenser, for spraying said wrinkle reducing composition on fabric, wherein said spray dispenser is capable of dispensing onto said fabric an amount of said wrinkle reducing active of from about 0.1% to about 4%, by weight of said fabric; and
  wherein said wrinkle reducing composition is substantially free of starch, modified starch, and mixtures thereof; and wherein said wrinkle reducing composition results in a Loss Modulus Difference of greater than about $3.3 \times 10^7$ Pascal on fabric to provide acceptable wrinkle reducing properties.

29. An article of manufacture, which comprises:
  A. a wrinkle reducing composition, comprising:
   1. a film-forming polymer selected from the group consisting of adipic acid/dimethylaminohydroxypropyl diethylenetriamine copolymer; adipic acid/epoxypropyl diethylenetriamine copolymer; poly(vinylpyrrolidone/dimethylaminoethyl methacrylate); polyvinyl alcohol; polyvinylpyridine n-oxide; methacryloyl ethyl betaine/methacrylates copolymer; ethyl acrylate/methyl methacrylate/methacrylic acid/acrylic acid copolymer; polyamine resins; polyquaternary amine resins; poly(ethyleneformamide); poly(vinylamine) hydrochloride; poly(vinyl alcohol-co-vinylamine); poly(vinyl alcohol-co-6% vinylamine); poly(vinyl alcohol-co-12% vinylamine); poly(vinyl alcohol-co-6% vinylamine hydrochloride); and poly(vinyl alcohol-co-12% vinylamine hydrochloride)
   2. an ethoxylated surfactant;
   3. an antistatic agent; and
   4. water; and
  B. a trigger-spray dispenser; and
  wherein said wrinkle reducing composition is substantially free of starch, modified starch, and mixtures thereof.

30. The article of manufacture of claim 27 wherein said film-forming polymer is present at a level of from about 0.1% to about 4.5%, by weight of the composition.

31. The method of reducing wrinkles in fabric, which comprises spraying an effective amount of wrinkle reducing composition onto a wrinkled portion of fabric with the article of manufacture of claim 1, wherein said fabric is not sprayed to saturation and hanging said fabric until it is dry.

32. The method of claim 29 wherein said wrinkled portion of said fabric is stretched perpendicular to the wrinkle or smoothed by hand before hanging said fabric.

33. The method of reducing wrinkles in fabric, which comprises spraying an effective amount of said composition onto a wrinkled portion of fabric with the article of manufacture of claim 1, wherein said fabric is not sprayed to saturation and ironing said fabric.

* * * * *